(12) United States Patent
Tanaka et al.

(10) Patent No.: US 10,787,479 B2
(45) Date of Patent: Sep. 29, 2020

(54) CRYSTALLINE 3',5'-CYCLIC DIGUANYLIC ACID

(71) Applicant: Yamasa Corporation, Choshi-shi (JP)

(72) Inventors: Hisaki Tanaka, Choshi (JP); Kazuya Ishige, Choshi (JP)

(73) Assignee: Yamasa Corporation, Choshi-shi (JP)

(*) Notice: Subject to any disclaimer, the term of this patent is extended or adjusted under 35 U.S.C. 154(b) by 0 days.

(21) Appl. No.: 16/441,484

(22) Filed: Jun. 14, 2019

(65) Prior Publication Data

US 2019/0315795 A1    Oct. 17, 2019

Related U.S. Application Data

(62) Division of application No. 15/123,328, filed as application No. PCT/JP2015/055975 on Feb. 27, 2015, now abandoned.

(30) Foreign Application Priority Data

Mar. 3, 2014   (JP) ................................ 2014-040108

(51) Int. Cl.
| | | |
|---|---|---|
| *C07H 19/207* | (2006.01) | |
| *C07H 19/213* | (2006.01) | |
| *C07H 1/00* | (2006.01) | |

(52) U.S. Cl.
CPC ............. *C07H 19/207* (2013.01); *C07H 1/00* (2013.01); *C07H 19/213* (2013.01)

(58) Field of Classification Search
CPC ....... C07H 1/00; C07H 19/207; C07H 19/213
USPC ...................................................... 536/26.12
See application file for complete search history.

(56) References Cited

U.S. PATENT DOCUMENTS

| | | |
|---|---|---|
| 2006/0167241 A1 | 7/2006 | Hayakawa |
| 2008/0286296 A1 | 11/2008 | Ebensen et al. |
| 2009/0169609 A1 | 7/2009 | Ebensen et al. |
| 2012/0040403 A1 | 2/2012 | Liang et al. |
| 2012/0164107 A1 | 6/2012 | Portnoy et al. |
| 2015/0044724 A1 | 2/2015 | Tanabe et al. |
| 2017/0096439 A1 | 4/2017 | Tanaka et al. |
| 2017/0101432 A1 | 4/2017 | Tanaka et al. |

FOREIGN PATENT DOCUMENTS

| | | | |
|---|---|---|---|
| CN | 102199183 A | 9/2011 | |
| EP | 1645561 A1 | 4/2006 | |
| WO | WO-2007/054279 A2 | 5/2007 | |
| WO | WO 2010/101526 A1 * | 9/2010 | ........... C07H 19/213 |
| WO | WO-2010/101526 A1 | 9/2010 | |
| WO | WO-2013/129427 A1 | 9/2013 | |

OTHER PUBLICATIONS

Liaw et al, FEBS, 1990, 264(2), 223-227.*
Caira, Topics in Current Chemistry, 1998, 198, 163-208.*
Frederick et al, Biochemistry, 1988, 27, 8350-61.*
Amiot et al., "New approach for the synthesis of c-di-GMP and its analogues," Synthesis. 24:4230-6 (2006).
Ault, Separation of Substances, *Techniques and Experiments for Organic Chemistry: Fifth Edition*. Waveland Press, Inc., 44-54 (1987).
Caira, "Crystalline polymorphism of organic compounds," Topics in Current Chemistry. 198:163-208 (1998).
Chen et al., "The potential of 3',5'-cyclic diguanylic acid (c-di-GMP) as an effective vaccine adjuvant," Vaccine. 28(18):3080-5 (2010).
Egli et al., "Atomic-resolution structure of the cellulose synthase regulator cyclic diguanylic acid," Proc Natl Acad Sci USA. 87(8):3235-9 (1990).
Extended European Search Report dated Jan. 25, 2017 for European Patent Application No. 15759144.7, Tanaka et al., "Crystalline 3',5'-cyclic Diguanylic Acid," filed Feb. 27, 2015 (10 pages).
Gaffney et al., "One-flask syntheses of c-di-GMP and the [Rp,Rp] and [Rp,Sp] thiophosphate analogues," available in PMC Jul. 16, 2011, published in final edited form as: Org Lett. 12(14):3269-71 (2010) (5 pages).
Guan et al., "Molecular structure of cyclic diguanylic acid at 1 Å resolution of two crystal forms: self-association, interactions with metal ion/planar dyes and modeling studies," J Biomol Struct Dyn. 11(2):253-76 (1993).
International Search Report for International Patent Application No. PCT/JP2015/055975, dated Apr. 21, 2015 (5 pages).
Ishige, Bioscience & Industry. 70(6):466-7, Nov. 1, 2012 (3 pages).
Karaolis et al., "c-di-GMP (3'-5'-cyclic diguanylic acid) inhibits *Staphylococcus aureus* cell-cell interactions and biofilm formation," Antimicrob Agents Chemother. 49(3):1029-38 (2005).
Liaw et al., "Cyclic diguanylic acid behaves as a host molecule for planar intercalators," FEBS Lett. 264(2):223-7 (1990).
Office Action dated Apr. 6, 2018 for Korean Application No. 10-2016-7025780, Tanaka et al., "3'5'-crystalline 3'5'-cyclic diguanylic acid," filed Feb. 27, 2015 (9 pages).
Office Action dated Apr. 8, 2019 for Chinese Patent Application No. 201580010888.X, Tanaka et al., "Crystalline 3',5'-cyclic Diguanylic Acid," filed Feb. 27, 2015 (14 pages).
Office Action dated Sep. 18, 2017 for Canadian Application No. 2,941,353, Tanaka et al., "Crystalline 3',5'-Cyclic Diguanyic Acid," filed Feb. 27, 2015 (6 pages).
Office Action dated Sep. 30, 2018 for Chinese Patent Application No. 201580010888, Tanaka et al., "Crystalline 3',5'-cyclic Diguanylic Acid," filed Feb. 27, 2015 (11 pages).
Ohtsuka et al., "Studies on transfer ribonucleic acids and related compouns. VII. Synthesis and properties of cyclic oligoadenylic acids," Chem Pharm Bull. 22(5):1022-8 (1974).
Written Opinion for International Patent Application No. PCT/JP2015/055975, dated Apr. 21, 2015 (7 pages).

(Continued)

*Primary Examiner* — Ganapathy Krishnan
(74) *Attorney, Agent, or Firm* — Clark & Elbing LLP; Susan M. Michaud (57) ABSTRACT

A crystal of free acid of 3',5'-cyclic diguanylic acid containing no metal salt with cobalt, magnesium or the like is provided. A method is sought for obtaining said crystal in a large amount and with ease. By a manufacturing method comprising a step of adding acid to an aqueous solution of 3',5'-cyclic diguanylic acid so as to lower pH to 1 to 3, crystals of 3',5'-cyclic diguanylic acid can be obtained in a large amount with ease. Said crystals are free acid crystals which do not contain a metal salt with cobalt, magnesium or the like.

6 Claims, 6 Drawing Sheets

(56) References Cited

OTHER PUBLICATIONS

Xiao, *Principles of Microbial Engineering*, China Light Industry Press, 292-8 (2004) (8 pages).

Yan et al., "Synthesis of 3',5'-cyclic diguanylic acid (cdiGMP) using 1-(4-chlorophenyl)-4-ethoxypiperidin-4-yl as a protecting group for 2'-hydroxy functions of ribonucleosides," Nucleosides, Nucleotides, and Nucleic Acids. 26(2):189-204 (2007).

Zhang et al., "c-di-GMP displays a monovalent metal ion-dependent polymorphism," J Am Chem Soc. 126(51):16700-1 (2004).

Hirayama, Yuki Kagobutsu Kessho Sakusei Handbook, pp. 17-23, 37-40, 45-51, 57-65 (2008) (44 pages).

Caira, "Crystalline polymorphism of organic compounds." *Topics in Current Chemistry*, vol. 198. Springer Verlag, 163-208 (1998).

Extended European Search Report for European Patent Application No. 15761774.7 dated Dec. 21, 2016, Tanaka et al., "Inclusion compound of 3',5'-cyclicdiadenylic acid, and method for producing same," filed Mar. 12, 2015 (8 pages).

Gaffney et al., "Synthesis of biotinylated c-di-GMP and c-di-AMP using click conjugation," Nucleosides Nucleotides Nucleic Acids. 32(1):1-16 (2013).

International Search Report for International Patent Application No. PCT/JP2015/057386, dated Apr. 7, 2015 (7 pages).

Kamegaya et al., "Identification of a *Streptococcus pyogenes* SF370 gene involved in production of c-di-AMP," Nagoya J Med Sci. 73(1-2):49-57 (2011).

Takata, "Soyaku Dankai ni Okeru Gen'yaku Form Screening to Sentaku: API form screening and selection in drug discovery stage," Pharm Stage. 6(10):20-5 (2007) (19 pages).

Witte et al., "Structural biochemistry of a bacterial checkpoint protein reveals diadenylate cyclase activity regulated by DNA recombination intermediates," Mol Cell. 30(2):167-78 (2008).

Woodward et al., "c-di-AMP secreted by intracellular *Listeria monocytogenes* activates a host type I interferon response," Science. 328(5986):1703-5 (2010).

\* cited by examiner

CRYSTALLINE 3',5'-CYCLIC DIGUANYLIC ACID

TECHNICAL FIELD

The present invention is related to a crystal of 3',5'-cyclic diguanylic acid deemed to be a useful substance as an adjuvant and to a manufacturing method of said crystal.

BACKGROUND

3',5'-Cyclic diguanylic acid is a signal transmitter involved in biofilm formation of bacteria or the like, and recently, expected in applications as an adjuvant, an antiviral agent, and an anticancer agent (Non-Patent Document 1). As a manufacturing method of 3',5'-cyclic diguanylic acid, a synthetic method by an enzyme is known thus far, in which diguanylate cyclase from Genus *Geobacillusis*, for example, is used (Patent Document 1).

Conventionally, 3',5'-cyclic diguanylic acid is obtained as a freeze-dried product or a co-crystal with a metal salt with cobalt or magnesium (Non-Patent Documents 2 and 3).

PRIOR ART DOCUMENTS

Patent Documents

Patent Document 1: PCT International Publication No. WO 2013-129427

Non-Patent Documents

Non-Patent Document 1: Vaccine, 28, 3080-3085 (2010)
Non-Patent Document 2: Proc. Natl. Acad. Sci. USA, 87, 3235-3239 (1990)
Non-Patent Document 3: FEBS Letters, 264, 223-227 (1990)

SUMMARY

Problems to be Solved by the Invention

Conventionally, 3',5'-cyclic diguanylic acid is provided as co-crystals containing a metal salt with cobalt or the like, and thus, in a case where the crystals are intended for utilization in a pharmaceutical raw material and the like, problems concerning safety or the like may arise. However, for crystals of free acid of 3',5'-cyclic diguanylic acid that do not contain the metal salt, nothing is conventionally known including methods of obtaining them. Further, all of conventional methods of obtaining crystals employ the vapor diffusion method, so that they are not suitable for obtaining a large amount of crystals in a short period of time, and thus, development of a method of obtaining a large amount of crystals easily has been desired.

Means to Solve the Problems

The present inventors studied earnestly crystallization of 3',5'-cyclic diguanylic acid and succeeded in obtaining crystals of the free acid of 3',5'-cyclic diguanylic acid for the first time.

Further, as for a manufacturing method of the crystals, it was also found newly that preparation is possible by adding acid to an aqueous solution of 3',5'-cyclic diguanylic acid so as to lower pH to 1 to 3, which is a very simple and easy step as compared with manufacturing methods of the conventional co-crystals with a metal salt.

Advantageous Effect of the Invention

The crystals of 3',5'-cyclic diguanylic acid obtained by the method of the present invention exhibit stability comparable to the existing crystals, and are very easy to handle in various applications, since no superfluous metal ions are included, and thus, useful as a raw material of pharmaceutical compositions and the like.

DETAILED DESCRIPTION OF PREFERRED EMBODIMENTS

The present invention provides a crystal of 3',5'-cyclic diguanylic acid represented by the following structural formula.

The crystal of 3',5'-cyclic diguanylic acid of the present invention is a crystal of free acid containing no metal salt, which is obtained without utilizing a metal such as cobalt and magnesium at all in a crystalizing step. Note that a 'crystal of 3',5'-cyclic diguanylic acid' in this description means a crystal of free acid containing none of said metal salts, unless specifically mentioned.

The crystal of 3',5'-cyclic diguanylic acid of the present invention has purity of 97% or more or preferably 99% or more as purity-tested by the high-performance liquid chromatography method.

The crystal of 3',5'-cyclic diguanylic acid of the present invention has water content of 9.3 to 13.9% as measured by the Karl Fischer method. That is, in the crystal of 3',5'-cyclic diguanylic acid of the present invention, 4 to 6 molecules of water, more specifically, 3.9 to 6.2 molecules of water bond or attach to one molecule of 3',5'-cyclic diguanylic acid.

The crystal of 3',5'-cyclic diguanylic acid of the present invention has an endothermic peak at 213 to 217° C. as analyzed by a thermogravimetric measurement/differential thermal analysis (TG/DTA) apparatus (temperature elevation rate of 5° C./min). Said temperature is lower than those of the known co-crystals with a metal.

The crystal of 3',5'-cyclic diguanylic acid of the present invention is obtained as a cubic crystal. In contrast, the conventionally known co-crystals with a metal are a hexagonal tabular crystal or a square bipyramidal crystal, and thus, the crystal of the present invention and the conventionally known co-crystals with a metal are different in structure.

The crystal of 3',5'-cyclic diguanylic acid of the present invention has characteristic peaks around 3163, 1712, 1637, 1601, 1530, 1470, 1386 and 1339 ($cm^{-1}$) when an infrared absorption spectrum is measured.

Note that generally an error range less than 2 ($cm^{-1}$) is sometimes included in measuring an infrared absorption spectrum, so that not only crystals whose peak positions in an infrared absorption spectrum coincide exactly with the values noted above but also crystals whose peak positions coincide within the error range less than 2 $cm^{-1}$ are included in the crystal of 3',5'-cyclic diguanylic acid of the present invention. For example, when an infrared absorption spectrum is measured, characteristic peaks are observed at 3163±1.9, 1712±1.9, 1637±1.9, 1601±1.9, 1530±1.9, 1470±1.9, 1386±1.9 and 1339±1.9 ($cm^{-1}$).

The crystal of 3',5'-cyclic diguanylic acid of the present invention has characteristic peaks in X-ray powder analysis, and, for example, when the crystal of the present invention is subjected to an analysis by an X-ray powder diffractometer using the Cu—Kα ray, characteristic peaks are observed, as shown in Example below, around 8.1, 8.3, 10.8, 11.8, 16.9, 19.1, 19.5, 22.4, 25.0, 26.7, 27.0 and 27.7(°) in diffraction angle (2θ) (see FIG. 10).

Note that generally an error range less than 5% is sometimes included in diffraction angle (2θ) of X-ray powder diffraction, so that not only crystals whose diffraction angles of peaks in X-ray powder diffraction coincide exactly but also crystals whose diffraction angles of peaks coincide within the error range less than 5% are included in the crystal of 3',5'-cyclic diguanylic acid of the present invention. For example, in X-ray powder diffraction, characteristic peaks are observed at 8.1±0.4, 8.3±0.4, 10.8±0.5, 11.8±0.5, 16.9±0.8, 19.1±0.9, 19.5±0.9, 22.4±1.1, 25.0±1.2, 26.7±1.3, 27.0±1.3 and 27.7±1.3(°) in diffraction angle (2θ).

The crystal of 3',5'-cyclic diguanylic acid of the present invention has a decreasing rate of purity less than 1% as a value measured by high performance liquid chromatography after being stored at 50° C. for 167 days in a desiccator containing saturated saline, and thus, is a very stable crystal.

The crystal of 3',5'-cyclic diguanylic acid of the present invention can be obtained by adding acid to an aqueous solution of 3',5'-cyclic diguanylic acid so as to lower pH to 1 to 3.

3',5'-Cyclic diguanylic acid used in crystallization may be synthesized by a known method such as the enzymatic synthesis method or the chemical synthesis method, and one synthesized by the enzymatic synthesis method is preferable. Enzymatic synthesis may be performed following the known method, and, for example, the method described in Patent Document 1 may be used. After the reaction, 3',5'-cyclic diguanylic acid generated in a reaction solution can be isolated and purified by the usual chromatography method using activated carbon, an ion-exchange resin or the like.

In crystallization, acid is added to an aqueous solution of 3',5'-cyclic diguanylic acid so as to lower pH to 1 to 3, preferably, to 1.5 to 2.0. Examples of the acid used are hydrochloric acid, sulfuric acid and nitric acid. In order to prevent amorphism or rapid crystal precipitation from being caused by adding acid rapidly, slow addition is preferable. Note that if a yield of crystals is low, second crystals may be obtained from the filtrate of said crystals by performing said process of crystal precipitation.

Further, crystallization may be performed by a method comprising (1) a step of heating an aqueous solution of isolated and purified 3',5'-cyclic diguanylic acid to 50 to 70° C., (2) a step of adding acid to said solution so as to lower pH to 1 to 3, preferably to 1.5 to 2.0, and (3) a step of cooling said solution until the solution reaches 1 to 10° C., preferably 4 to 8° C. In order to ensure crystal precipitation, it is preferable that cooling in step (3) is performed slowly. Specifically, cooling with a temperature gradient of −3 to −11° C./hr is preferable. Further, steps (1) and (2) or steps (2) and (3) may be performed simultaneously.

The crystals of 3',5'-cyclic diguanylic acid obtained by the manufacturing method described above may be collected by filtration and then dried at 30 to 70° C. for 1 to 10 hours, to be a product. In drying, an appropriate method may be employed such as drying under reduced pressure.

EXAMPLES

Hereafter, examples will be shown to explain the present invention specifically, however, it is apparent that the present invention is not limited thereto.

Example 1

Manufacture of Crystals of 3',5'-cyclic diguanylic acid

3',5'-Cyclic diguanylic acid was synthesized enzymatically and purified according to a known method (Patent Document 1).

A 59.9 mM solution (191 mL) of 3',5'-cyclic diguanylic acid obtained by purification was warmed to 60° C. in an incubator and 27.5 mL of 1 N hydrochloric acid solution was added while stirring over two hours so as to make pH at 1.9.

After the addition of the hydrochloric acid solution, cooling was performed using a programmable incubator with a temperature gradient of −7° C./hr until the temperature of the solution reached 5° C. to cause crystals to precipitate. The crystals thus precipitated were collected with a glass filter (17G3) to obtain wet crystals. The wet crystals were dried at 30° C. for 9 hours and 8.095 g of dry crystals were obtained.

Reference Example

Manufacture of Co-Crystals of 3',5'-cyclic diguanylic acid with Metal

Co-crystals of 3',5'-cyclic diguanylic acid with magnesium or cobalt were obtained in the following manner with reference to the descriptions of Non-Patent Documents 2 and 3.

Reference Example 1

Co-Crystals of 3',5'-cyclic diguanylic acid with Magnesium 500 mL of a starting solution for crystallization (2 mM 3',5'-cyclic diguanylic acid, 20 mM $MgCl_2$, 20 mM glycine-HCl (pH 2.1), 7% (v/v) 2-MPD) was prepared.

The starting solution for crystallization was concentrated by an evaporator while being warmed at 55° C., filled up to 500 mL again at the time white turbidity was observed, and warmed at 55° C. for 30 minutes to achieve complete dissolution. The solution was concentrated again, allowed to clarify, and left to stand overnight at 25° C., in which precipitation of hexagonal tabular crystals were observed, so that the crystals were grown sufficiently by the vapor diffusion method to obtain co-crystals with magnesium.

Reference Example 2

Co-Crystals of 3',5'-cyclic diguanylic acid with Cobalt 500 mL of a starting solution for crystallization (2 mM 3',5'-cyclic diguanylic acid, 11 mM $CoCl_2$, 20 mM glycine-HCl (pH 2.1), 7% (v/v) 2-MPD) was prepared.

The starting solution for crystallization was concentrated by an evaporator while being warmed at 55° C. and left to stand overnight at 25° C., in which precipitation of square bipyramidal crystals were observed, so that the crystals were grown by the vapor diffusion method. In the vapor diffusion method, 800 mL of 50% 2-MPD (water:MPD=1:1) was placed in an airtight container (TLC developing vessel) and both beakers were left to stand therein for 6 months to obtain co-crystals with cobalt.

Example 2

Physical Properties of Crystals of 3',5'-cyclic diguanylic acid

Figure 1:
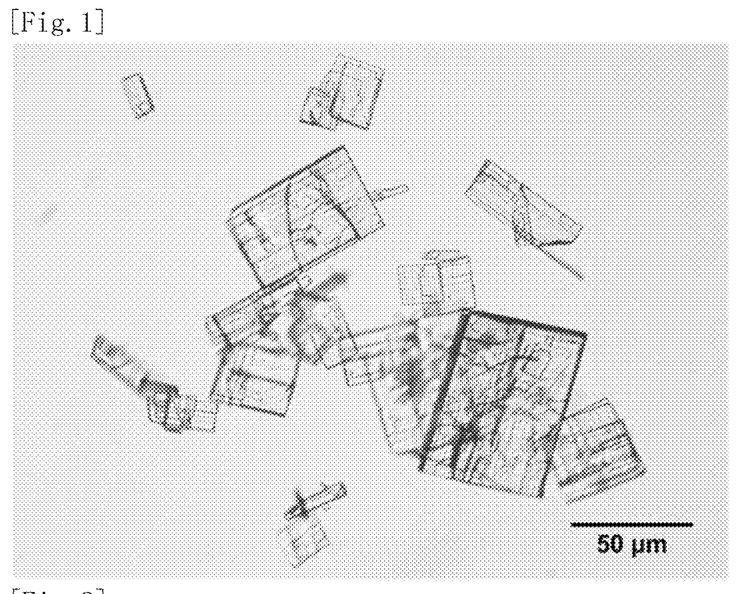
FIG. 1 shows a photograph of crystals of 3',5'-cyclic diguanylic acid.
Figure 2:
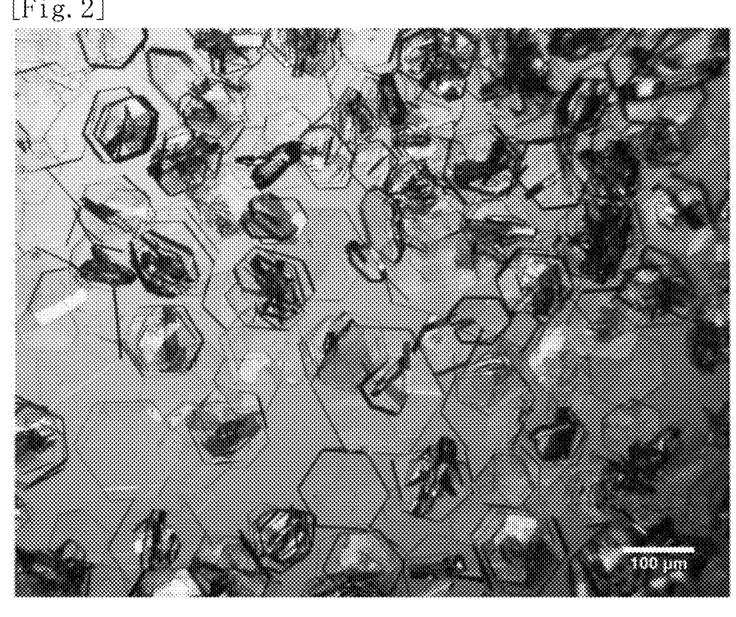
FIG. 2 shows a photograph of co-crystals of 3',5'-cyclic diguanylic acid with magnesium.
Figure 3:
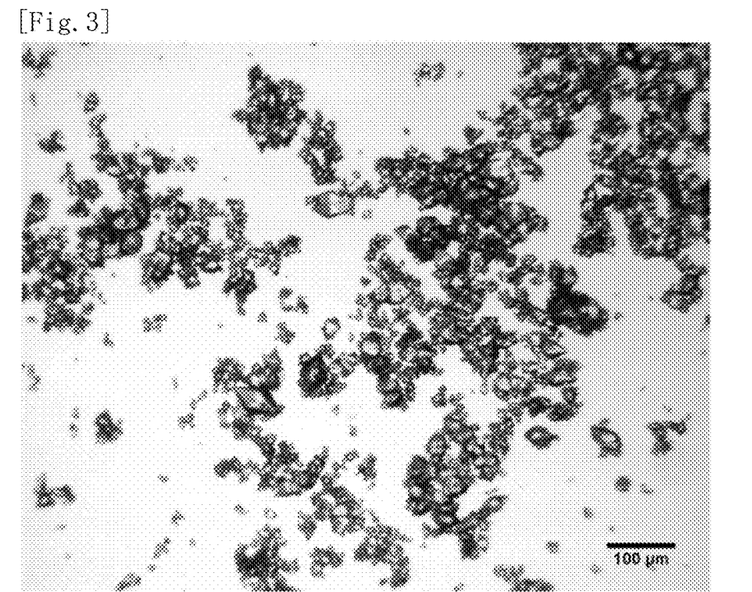
FIG. 3 shows a photograph of co-crystals of 3',5'-cyclic diguanylic acid with cobalt.

Instrumental analyses were performed on the crystals of 3',5'-cyclic diguanylic acid prepared in Example 1 above, whose results are shown below.
(Instrumental Analysis)
(A) Purity Test Purity of the crystals of 3',5'-cyclic diguanylic acid obtained in Example 1 was analyzed by the high performance liquid chromatography method and it was found that purity of 3',5'-cyclic diguanylic acid was 99.0%. Note that the high performance liquid chromatography method was performed under the following condition.
(Condition)
  Column: Hydrosphere C18 (product of YMC Co., Ltd.)
  Eluate: 0.1M TEA-P (pH 6.0)
  Detection method: detection by UV 260 nm (B) Crystalline Shape Representative photographs of the crystals of 3',5'-cyclic diguanylic acid prepared in Example 1 and the co-crystals of 3',5'-cyclic diguanylic acid with magnesium and the co-crystals with cobalt prepared in Reference Examples are shown in FIGS. 1 to 3. As shown in FIG. 1, the crystal of 3',5'-cyclic diguanylic acid of the present invention is a cubic crystal, whereas, as shown in FIGS. 2 and 3, the co-crystal with magnesium is a hexagonal tabular crystal and the co-crystal with cobalt is a square bipyramidal crystal, and thus, the crystal of the present invention exhibited a completely different crystalline shape from those of the conventional crystals.

(C) Water Content

Water content of the crystals of 3',5'-cyclic diguanylic acid prepared in Example 1 was measured by the Karl Fischer method and water content was found to be 9.3 to 13.9%. That is, it was revealed that, in the crystal of 3',5'-cyclic diguanylic acid of the present invention, 4 to 6 molecules of water, more specifically, 3.9 to 6.2 molecules of water bonded or attached to one molecule of 3',5'-cyclic diguanylic acid.

(D) Differential Scanning Calorimetry

Figure 4:
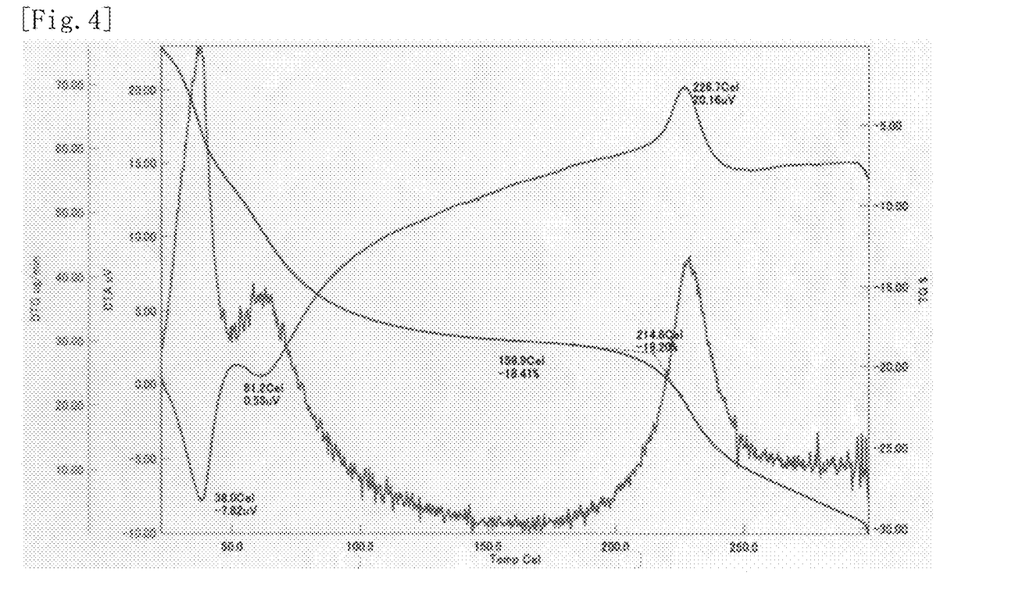
FIG. 4 shows a result of thermogravimetric measurement/differential thermal analysis of crystals of 3',5'-cyclic diguanylic acid.
Figure 5:
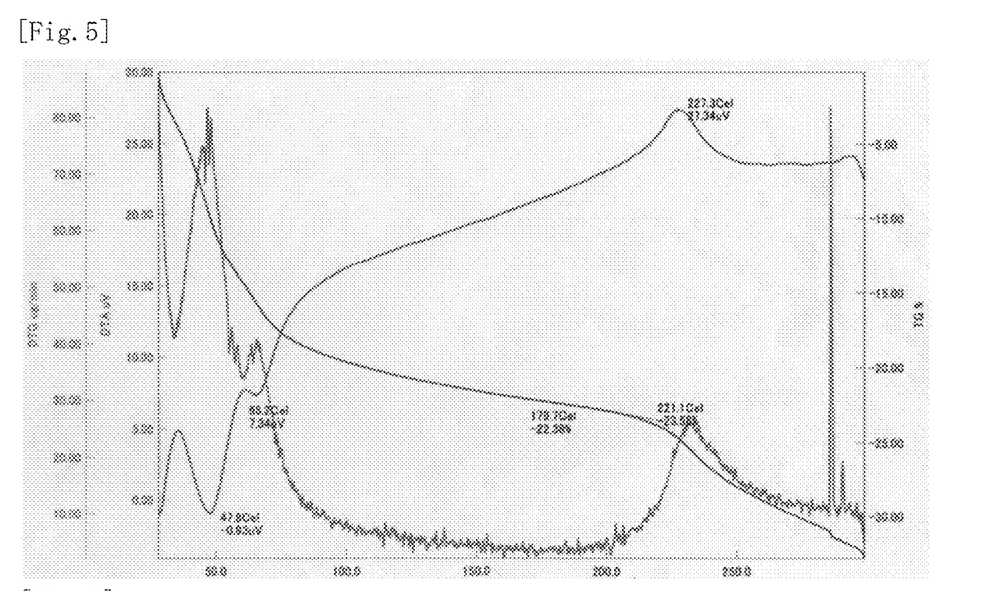
FIG. 5 shows a result of thermogravimetric measurement/differential thermal analysis of co-crystals of 3',5'-cyclic diguanylic acid with magnesium.
Figure 6:
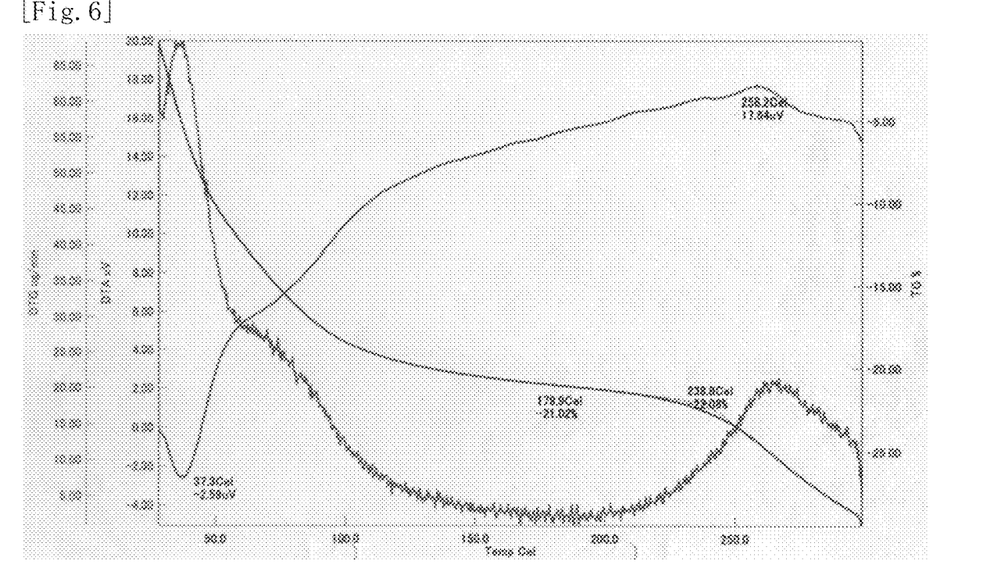
FIG. 6 shows a result of thermogravimetric measurement/differential thermal analysis of co-crystals of 3',5'-cyclic diguanylic acid with cobalt.

When analyzed by a thermogravimetric measurement/differential thermal analysis (TG/DTA) apparatus (temperature elevation rate of 5° C./min), the crystals of 3',5'-cyclic diguanylic acid of the present invention showed a characteristic endothermic peak at 213 to 217° C. (FIG. 4). In contrast, the co-crystals of 3',5'-cyclic diguanylic acid with magnesium showed a characteristic endothermic peak around 221° C. and co-crystals with cobalt showed a characteristic endothermic peak around 239° C. (FIGS. 5 and 6, respectively).

(E) Infrared Absorption Spectrometry

Infrared absorption spectrum was measured on each of the crystal of 3',5'-cyclic diguanylic acid of the present invention, and the co-crystal of 3',5'-cyclic diguanylic acid with magnesium and the co-crystal of 3',5'-cyclic diguanylic acid with cobalt of Reference Examples using a Fourier transform infrared spectrophotometer, Spectrum One (product of PerkinElmer Co., Ltd.) by the ATR (Attenuated Total Reflectance) method.

Figure 7:
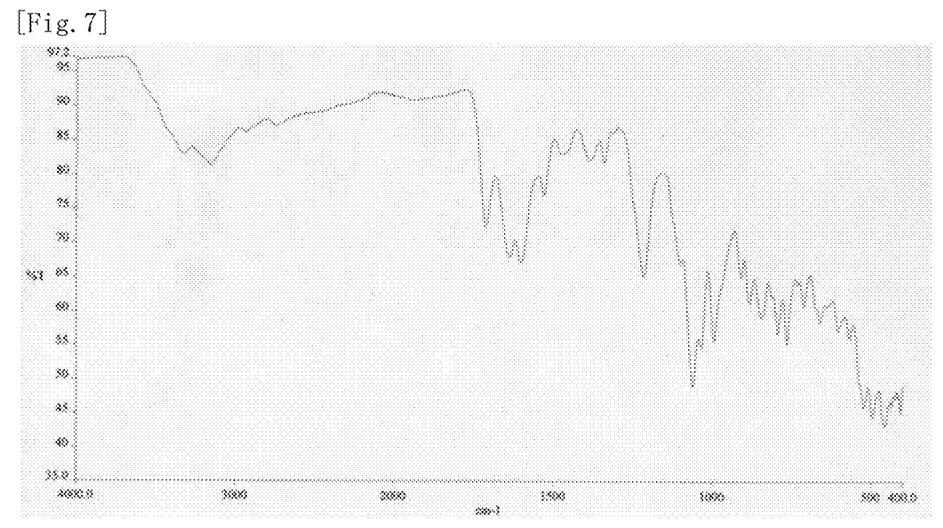
FIG. 7 shows an infrared absorption spectrum of crystals of 3',5'-cyclic diguanylic acid.
Figure 8:
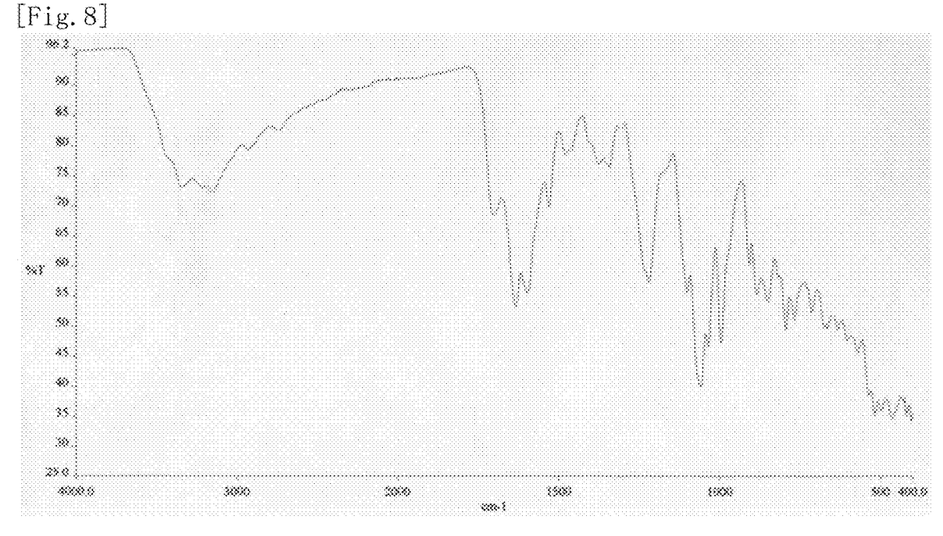
FIG. 8 shows an infrared absorption spectrum of co-crystals of 3',5'-cyclic diguanylic acid with magnesium.
Figure 9:
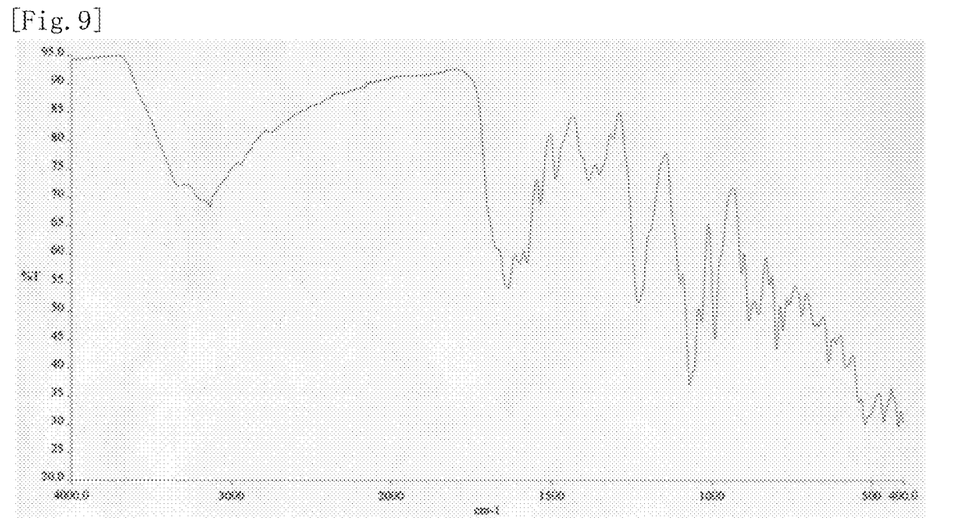
FIG. 9 shows an infrared absorption spectrum of co-crystals of 3',5'-cyclic diguanylic acid with cobalt.

The values of characteristic peaks ($cm^{-1}$) observed for each of the crystals are shown in Table 1. Further, infrared absorption spectra of the crystal of 3',5'-cyclic diguanylic acid of the present invention, the co-crystal of 3',5'-cyclic diguanylic acid with magnesium, and the co-crystal of 3',5'-cyclic diguanylic acid with cobalt are shown in FIGS. 7, 8 and 9, respectively.

The crystal of 3',5'-cyclic diguanylic acid of the present invention had characteristic peaks around 3163, 1712, 1637, 1601, 1530, 1470, 1386 and 1339 ($cm^{-1}$). In contrast, the co-crystal with magnesium had characteristic peaks around 3226, 1702, 1634, 1597, 1531, 1477 and 1345 ($cm^{-1}$) and the co-crystal with cobalt had characteristic peaks around 3179, 1638, 1576, 1534, 1487 and 1383 ($cm^{-1}$). These results are shown in Table 1.

TABLE 1

| Present invention ($cm^{-1}$) | Co-crystal with Mg ($cm^{-1}$) | Co-crystal with Co ($cm^{-1}$) |
|---|---|---|
| 3163 | 3226 | 3179 |
| 1712 | 1702 | |
| 1637 | 1634 | 1638 |
| 1601 | 1597 | |
| | | 1576 |
| 1530 | 1531 | 1534 |

TABLE 1-continued

| Present invention (cm$^{-1}$) | Co-crystal with Mg (cm$^{-1}$) | Co-crystal with Co (cm$^{-1}$) |
|---|---|---|
| 1470 | 1477 | 1487 |
| 1386 | | 1383 |
| 1338.79 | 1345 | |

(F) X-Ray Powder Diffractometry

X-ray diffraction spectra of the crystal of 3',5'-cyclic diguanylic acid of the present invention, and the co-crystal of 3',5'-cyclic diguanylic acid with cobalt and the co-crystal of 3',5'-cyclic diguanylic acid with magnesium of Reference Examples were measured using an X-ray diffractometer X'Pert PRO MPD (product of Spectris Co., Ltd.) under the following measurement condition.

(Measurement Condition)

Target: Cu

X-ray tube current: 40 mA

X-ray tube voltage: 45 kV

Scan range: 2θ=4.0 to 40.0°

Pretreatment: Pulverization using an agate mortar

Figure 10:
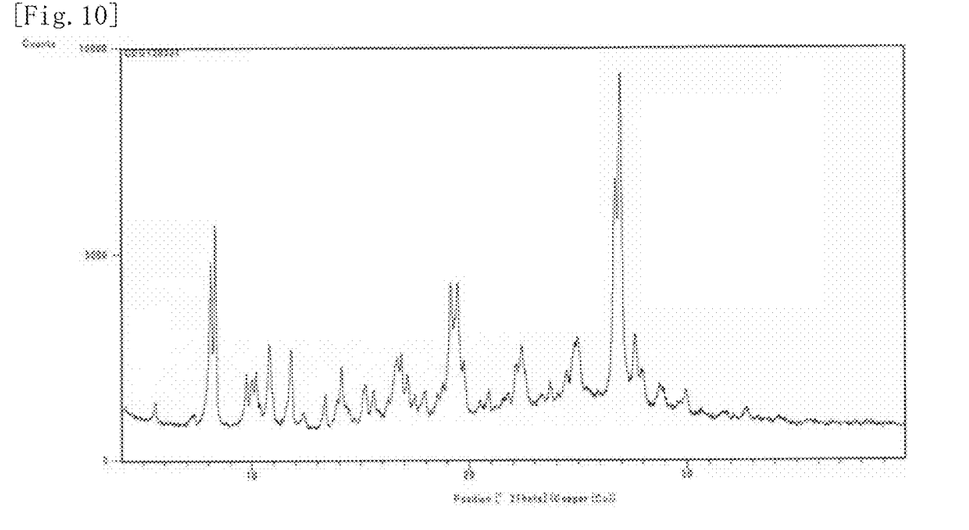
FIG. 10 shows an X-ray diffraction spectrum of crystals of 3',5'-cyclic diguanylic acid.
Figure 11:
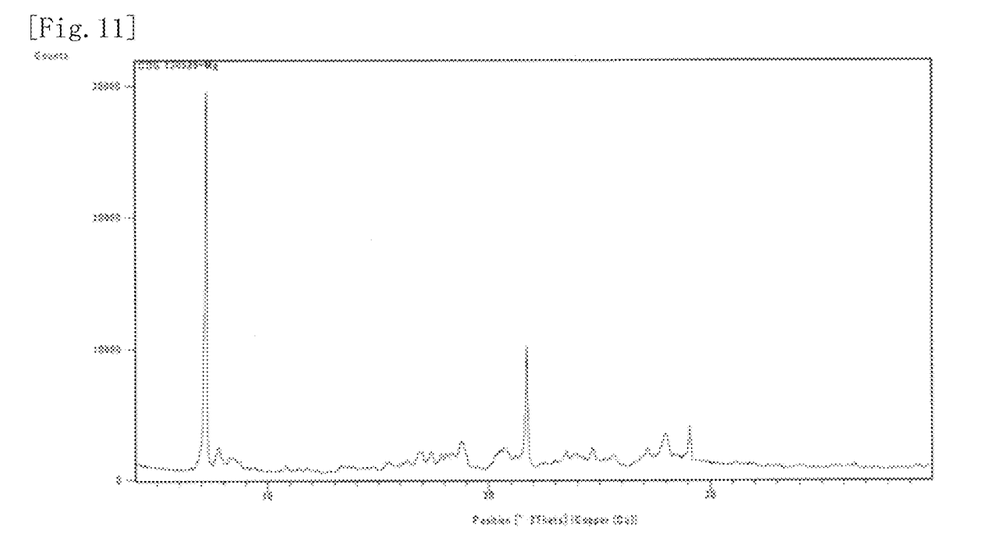
FIG. 11 shows an X-ray diffraction spectrum of co-crystals of 3',5'-cyclic diguanylic acid with magnesium.
Figure 12:
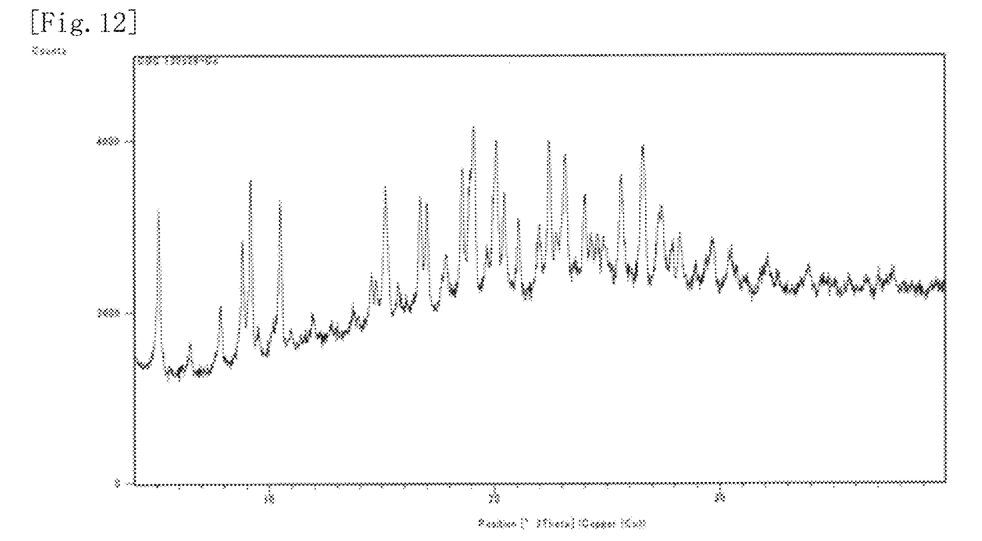
FIG. 12 shows an X-ray diffraction spectrum of co-crystals of 3',5'-cyclic diguanylic acid with cobalt.

As shown in FIG. 10 and Table 2, the crystal of 3',5'-cyclic diguanylic acid of the present invention showed characteristic peaks around 8.1, 8.3, 10.8, 11.8, 16.9, 19.1, 19.5, 22.4, 25.0, 26.7, 27.0 and 27.7(°) in diffraction angle (2θ). Note that, as comparative data, the result of the co-crystal of 3',5'-cyclic diguanylic acid with magnesium is shown in FIG. 11 and Table 3 and the result of the co-crystal of 3',5'-cyclic diguanylic acid with cobalt in FIG. 12 and Table 4.

TABLE 2

Present Invention

| 2θ (°) | Relative Intensity |
|---|---|
| 8.1 | 45.0 |
| 8.3 | 56.9 |
| 10.8 | 23.3 |
| 11.8 | 22.1 |
| 16.9 | 21.0 |
| 19.1 | 40.8 |
| 19.5 | 40.6 |
| 22.4 | 22.6 |
| 25.0 | 25.9 |
| 26.7 | 70.1 |
| 27.0 | 100 |
| 27.7 | 26.1 |

TABLE 3

Co-crystal with Mg

| 2θ (°) | Relative Intensity |
|---|---|
| 7.1 | 34.9 |
| 7.3 | 100 |
| 18.8 | 8.3 |
| 21.7 | 33.8 |
| 28.0 | 10.0 |
| 29.1 | 11.8 |

TABLE 4

Co-crystal with Co

| 2θ (°) | Relative Intensity |
|---|---|
| 5.1 | 75.0 |
| 8.8 | 58.8 |
| 9.2 | 88.7 |
| 10.5 | 74.4 |
| 15.2 | 75.1 |
| 16.7 | 69.7 |
| 17.0 | 66.8 |
| 18.6 | 79.2 |
| 19.1 | 100 |
| 20.1 | 91.6 |
| 20.5 | 68.3 |
| 22.4 | 90.5 |
| 23.2 | 82.1 |
| 24.0 | 61.0 |
| 25.7 | 70.2 |
| 26.7 | 80.7 |

(G) Stability

The crystals of 3',5'-cyclic diguanylic acid of the present invention and the co-crystals with cobalt and the co-crystals with magnesium of Reference Examples were stored at 50° C. in a desiccator containing saturated saline, and HPLC purity of each of them was measured on days 0, 7, 31, 84 and 167 after the start of storage. The result of measurement of HPLC purity (%) is shown in Table 5 below and relative residual ratios (%) on each day for measurement after the start of storage, taking the purity of day 0 of measurement as 100%, are shown in Table 6.

As a result, a decrease rate of HPLC purity of 3',5'-cyclic diguanylic acid of the present invention is less than 1% after storing at 50° C. for 167 days, showing a very high stability. This value is comparable with those of the conventional co-crystals with a metal, meaning that practical use is possible.

TABLE 5

| (Days) | 0 | 7 | 31 | 84 | 167 |
|---|---|---|---|---|---|
| Present Invention (%) | 99.0 | 99.1 | 98.6 | 98.9 | 98.9 |
| Mg (%) | 99.8 | 99.7 | 99.6 | 99.8 | 99.3 |
| Co (%) | 99.9 | 99.9 | 99.7 | 99.7 | 99.4 |

TABLE 6

| (Days) | 0 | 7 | 31 | 84 | 167 |
|---|---|---|---|---|---|
| Present Invention (%) | 100 | 100.1 | 99.6 | 99.9 | 100.0 |
| Mg (%) | 100 | 100 | 99.8 | 100.0 | 99.5 |
| Co (%) | 100 | 100 | 99.8 | 99.8 | 99.6 |

What is claimed is:

1. A crystal of 3',5'-cyclic diguanylic acid, wherein characteristic peaks are observed around 8.1, 8.3, 10.8, 11.8, 16.9, 19.1, 19.5, 22.4, 25.0, 26.7, 27.0 and 27.7 (°) in diffraction angle (2θ) in X-ray powder analysis, and the crystal of 3',5'-cyclic diguanylic acid is a crystal of free acid containing no metal salts.

2. The crystal of claim 1 having purity of 97% or more as measured by high-performance liquid chromatography.

3. The crystal of claim 1 having purity of 99% or more as measured by high-performance liquid chromatography.

4. The crystal of claim 1, wherein approximately 4 to 6 molecules of water bond or attach to one molecule of 3',5'-cyclic diguanylic acid.

5. The crystal of claim 1, wherein an endothermic peak is observed at 213 to 217° C. as measured by a thermogravimetric measurement/differential thermal analysis (TG/DTA) apparatus.

6. The crystal of claim 1, wherein characteristic peaks are observed around 3163, 1712, 1637, 1601, 1530, 1470, 1386 and 1339 (cm$^{-1}$) when an infrared absorption spectrum is measured.

\* \* \* \* \*